(12) United States Patent
Souzy et al.

(10) Patent No.: US 9,775,795 B2
(45) Date of Patent: *Oct. 3, 2017

(54) COPOLYMERS IN COSMETIC COMPOSITIONS

(71) Applicant: COATEX, Genay (FR)

(72) Inventors: Renaud Souzy, Caluire et Cuire (FR); Yves Kensicher, Theize (FR); Jean-Marc Suau, Lucenay (FR); Olivier Guerret, Pern (FR)

(73) Assignee: COATEX, Genay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,582

(22) PCT Filed: Sep. 24, 2013

(86) PCT No.: PCT/FR2013/052233
§ 371 (c)(1),
(2) Date: Mar. 19, 2015

(87) PCT Pub. No.: WO2014/053743
PCT Pub. Date: Apr. 10, 2014

(65) Prior Publication Data
US 2015/0231054 A1    Aug. 20, 2015

Related U.S. Application Data

(60) Provisional application No. 61/708,733, filed on Oct. 2, 2012.

(30) Foreign Application Priority Data

Oct. 2, 2012  (FR) ..................... 12 02617
Jun. 28, 2013 (FR) ..................... 13 56252

(51) Int. Cl.
*A61K 8/81*   (2006.01)
*A61K 8/19*   (2006.01)
*A61K 8/87*   (2006.01)
*A61Q 1/10*   (2006.01)

(52) U.S. Cl.
CPC .............. *A61K 8/8147* (2013.01); *A61K 8/19* (2013.01); *A61K 8/8135* (2013.01); *A61K 8/8182* (2013.01); *A61K 8/87* (2013.01); *A61Q 1/10* (2013.01); *A61K 2800/432* (2013.01); *A61K 2800/54* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 8,778,368 B2* | 7/2014 | Suau | .................... A61K 8/8152 424/401 |
| 2003/0019401 A1 | 1/2003 | Schwartz et al. | |
| 2007/0082979 A1 | 4/2007 | Villard et al. | |
| 2009/0182061 A1 | 7/2009 | Moro et al. | |
| 2010/0233114 A1* | 9/2010 | DeGeorge | .............. A61K 8/585 424/70.121 |
| 2010/0273923 A1 | 10/2010 | Suau et al. | |
| 2012/0230920 A1* | 9/2012 | Souzy et al. | .................... 424/47 |
| 2012/0251474 A1* | 10/2012 | Suau | ........................ A61K 8/91 424/70.16 |

FOREIGN PATENT DOCUMENTS

| | | |
|---|---|---|
| FR | 2 861 399 | 4/2005 |
| FR | 2 900 930 | 11/2007 |
| FR | 2 926 558 | 7/2009 |
| WO | 02 083594 | 10/2002 |

OTHER PUBLICATIONS

International Search Report Issued Nov. 25, 2013 in PCT/FR13/052233 Filed Sep. 24, 2013.

* cited by examiner

*Primary Examiner* — Brian Gulledge
(74) *Attorney, Agent, or Firm* — Oblon, McClelland, Maier & Neustadt, L.L.P.

(57) ABSTRACT

The present invention concerns the use of a specific copolymer to homogenize compositions that include coloring pigments and/or pearlescent pigments and film-forming polymers, as well as the cosmetic compositions containing said copolymer.

21 Claims, No Drawings

COPOLYMERS IN COSMETIC COMPOSITIONS

FIELD OF THE INVENTION

This invention concerns the cosmetic technical area, specifically the area of cosmetic compositions for coating keratinous fibers. More specifically, this invention concerns the use of a specific copolymer to homogenize compositions that include coloring pigments and/or pearlescent pigments and film-forming polymers, as well as the cosmetic compositions containing said copolymer.

BACKGROUND OF THE INVENTION

The cosmetic compositions intended to coat keratinous fibers, whose purpose in generally makeup and/or care, traditionally comprise coloring material such as mineral pigments, for example. In addition, the cosmetic compositions intended to coat keratinous fibers and which must be resistant to water, steam, humidity, sebum, and tears (mascara formulations, for example) generally comprise a film-forming polymer. The person skilled in the art tries to control the rheological, particle size distribution, stability, and sensory parameters during the implementation, storage, and post-use of the cosmetic compositions and, more specifically, of the compositions for coating keratinous fibers that comprise mineral or organic fillers, notably mineral pigments. For this purpose, they use dispersing additives or dispersing agents.

These dispersing agents are capable of dispersing the mineral pigments, for example metal oxide pigments such as iron oxide, in the compositions that contain them. In fact, a dispersing agent is typically used in order to prevent the flocculation of the particles and the ensuing loss of the desired properties. In practice, a dispersing agent included in a cosmetic formulation comprising metal pigments, leads to a viscosity lower than that of the same cosmetic formulation that does not contain said dispersing agent. The dispersing power of an agent in a formulation is thus measured by determining the viscosity. In addition, dispersing agents make it possible to stabilize the particle size distribution and texture parameters of the compositions. They make it possible to homogenize said compositions.

There are four broad categories of dispersing agents in cosmetic compositions: oils, surfactants, natural dispersants, and polymeric-type dispersants.

Additives of the cosmetic oils type, for example esters, such as the poly(hydroxystearic) acids, and some surfactants are commercially available for dispersing the iron oxides in cosmetic formulations for keratinous material. Nevertheless, these additives have the drawback of negatively impacting the sensory aspect of the compositions that include them; their use in these compositions is, therefore, limited.

Among the dispersants of natural or biosourced origin, one can mention the use of lignosulphonates and carbohydrates of the inulin type (Abstract of Paper, 244th ACS National Meeting & Exposition, Philadelphia, Aug. 19-23, 2012 Washington D.C.) and of acyl-poly(aminoacid), of poly-glutamate (US 20120076840 and JP 2012001503), and of poly(aspartic) acids. These natural dispersants have the drawback that they need to be purified in order to attain the molecular weight desired for optimum effectiveness as dispersing agents in cosmetic compositions.

A number of documents in the prior art discuss the dispersion of mineral filler pigments with polymeric additives.

One can cite, among them, *J. Cosmet. Sci.*, 50, 105-109, 1999, which concerns, in a general way, the water-based nail polish additives and which describes, notably, the implementation of water-soluble polymers as thickeners, stabilizers, and pigment dispersants. The homopolymers of ethylene oxide, of acrylic acid, of methacrylic acid, of polyvinyl alcohol, and of various cellulosic materials are examples of these additives.

One can also cite the article *Tenside Surf. Det.*, 36, 1999, which discusses a technical area different than that of this invention. This document describes the impact of polymeric and non-polymeric materials on the dispersion of iron oxide particles in the water used in industrial processes (for example in heat exchangers and distillation systems). The following polymers are specifically mentioned: polymers of acrylic acid, methacrylic acid, maleic acid, acrylamide, 2-acrylamido-2-methylpropane sulphonic acid, and copolymers of acrylic acid.

Patent WO 2009073384 describes the use of acrylic organosilylated copolymers. These commercially available copolymers have a non-negligible impact on the sensory and organoleptic properties of cosmetic formulations.

In addition, incompatibility problems are encountered in the cosmetic compositions which contain coloring mineral pigments of the metal oxide type, such as iron oxides, and which also comprise film-forming polymers and dispersing agents of the polymeric type. The simultaneous presence of two types of polymers within the cosmetic composition can, in some cases, lead to instability problems, such as dephasing or phase separation, bleeding, release, and deposition or sedimentation. This incompatibility becomes more important as the concentrations of pigments and/or film-forming polymers (also called agent or film-forming additive) are increased in said cosmetic compositions.

DESCRIPTION OF THE INVENTION

An object of this invention is to propose a polymeric additive that is compatible with the film-forming polymers used in the cosmetic compositions intended for coating water-resistant keratinous fibers, including the cases in which these film-forming polymers are present in high concentrations.

A further object of this invention is to propose a polymeric additive that makes it possible to efficiently disperse pearlescent pigments and/or coloring pigments used in said compositions, including when said pearlescent and/or pigments are present in high concentrations. A further object of this invention is to propose a copolymer that makes it possible to homogenize the cosmetic compositions that comprise film-forming polymers as well as over 1% and up to 20 wt. % of pearlescent and/or coloring pigments, specifically metal oxides such as iron oxides.

A further object of this invention is to propose a copolymer that makes the preparation of the cosmetic composition easier, for example by preventing caking and/or flocculation.

A further object of this invention is to propose a cosmetic composition intended to coat keratinous fibers which is resistant to water and which displays excellent stability on storage.

The inventors realized, to their surprise, that all these objectives are met by using a comb-type copolymer with a specific chemical composition and molecular weight.

In fact, the use of such a copolymer makes it possible to solve the incompatibility problems observed with film-forming polymers used in waterproof mascara-type cosmetic compositions; this enables the person skilled in the art, when preparing the formulation of her cosmetic composition, to solve problems such as, for example, caking, the formation of irreversible heterogeneities, and the precipitation of pigments when the various ingredients are added. Such a copolymer also makes it possible to homogenize the cosmetic compositions.

Moreover, the use of such a copolymer makes it possible to obtain cosmetic compositions that are more stable on storage, while maintaining the desired organoleptic properties.

This invention concerns the use of a water-soluble comb-type copolymer having a skeleton (principal chain) and side branches of polyalkylene glycol to homogenize cosmetic compositions that include a film-forming polymer and pearlescent and/or coloring pigments, in particular metal oxides such as iron oxide(s).

More specifically, the water-soluble copolymer is such that it comprises:
   at least one anionic monomer having a polymerizable vinyl group and a carboxyl moiety, such as (meth) acrylic acid;
   at least one monomer having a polymerizable unsaturated group, ethylene oxide (EU) units, and propylene oxide (PO) units, those EO and PO units potentially being randomly sequenced or regularly sequenced.

Moreover, the copolymer of the invention has a specific molecular weight between 20,000 and 400,000 g/mol, for example between 20,000 and 250,000 g/mol.

Thus, an object of this invention concerns the use of a copolymer made up of:
   a) at least one anionic monomer having a polymerizable vinyl group and a carboxyl moiety, such as (meth) acrylic acid, and
   b) at least one macro-monomer having the formula (I):

where: m and n are integers other than zero and lower than 150,
   PO and EO respectively designate propylene oxide and ethylene oxide and are arranged in a random or alternating block,
   R designates a polymerizable unsaturated group,
   R' is hydrogen or an alkyl group having 1, 2, 3, or 4 carbon atoms,
said copolymer having a molecular weight between 20,000 and 400,000 g/mol and homogenizing a cosmetic composition for makeup and/or for the care of keratinous material comprising a film-forming polymer and a pearlescent pigments and/or a coloring pigment.

Another object of this invention concerns a cosmetic composition for makeup and/or for the care of keratinous material, comprising:
   a) from 1 to 30 wt. % of pearlescent and/or coloring pigment;
   b) from 0.1 to 30 wt. % of film-forming polymer; and
   c) from 0.05 to 8 wt. % of comb-type copolymer formed of:
      c1) at least one anionic monomer having a polymerizable vinyl group and a carboxyl moiety, such as (meth)acrylic acid, and
      c2) at least one macro-monomer having the formula (I):

wherein:
   m and n are two integers other than zero and lower than 150;
   PO and EO designate respectively propylene oxide and ethylene oxide and are arranged either randomly or in a regular pattern;
   R designates a polymerizable unsaturated group;
   R' is hydrogen or an alkyl group having 1-4 carbon atoms;
   the molecular weight of said copolymer being between 20,000 g/mol and 400,000 g/mol.

Another object of this invention regards the use of a copolymer according to the invention to provide storage stability, as defined above, to a cosmetic composition for makeup and/or care of the keratinous material comprising a film-forming polymer and a pearlescent and/or coloring pigment, notably when the pearlescent and/or coloring pigment is present in a concentration between 1% and 30 wt. % relative to the total weight of the composition, and/or when the film-forming polymer is present in a concentration between 0.1% and 30 wt. % relative to the total weight of the composition.

Definitions

In the context of the present invention, the limits of the indicated ranges (wt. %, molecular weight, etc.) are included in the range.

"Pearlescent and/or coloring pigment" refers broadly to pulverulent coloring matters. These pulverulent coloring matters may be chosen from among pigments and pearlescent materials. The pigments may be white or colored, mineral and/or organic, coated or uncoated. Examples of mineral pigments include titanium dioxide, potentially surface-treated, zirconium oxides, zinc oxides, and cerium oxides, as well as iron or chromium oxides, manganese purple, ultramarine blue, chromium hydrate, and iron blue. Examples of organic pigments include carbon black, type D & C pigments, and lacquers made from cochineal carmine, barium, strontium, calcium, and aluminum. The pearlescent materials may be chosen from white pearlescent pigments such as mica covered with titanium or bismuth oxychloride, colored pearlescent pigments such as titanium mica with iron oxides, titanium mica particularly with iron blue or chromium oxide, titanium mica with an organic pigment of the aforementioned type as well as pearlescent pigments made from bismuth oxychloride.

In the context of the present invention, the term "coloring mineral pigment" means materials of mineral origin or obtained by a synthetic process, possibly chemically modified, which, once blended and coformulated in cosmetic compositions, make it possible to obtain cosmetic products of different colors or shades. The coloring pigment of the invention can be a synthetic mineral pigment.

In one embodiment of this invention, the coloring pigment is chosen from the group that includes iron oxides, chromium oxides, zirconium oxides, zinc or cerium oxides, manganese violet, blue ultramarine, chromium hydrate, carbon black, and iron blue.

In another embodiment of this invention, the coloring mineral pigment is an iron oxide or a mixture of iron oxides. The iron oxides are commercially available or custom produced.

"Film-forming polymer" means a polymer capable, by itself or in the presence of co-additives, of generating a continuous film which adheres to keratinous material. Preferably, this film is cohesive and can be isolated, if necessary. Synthetic polymers in the form of dispersions or emulsions of said polymers (in the form of a latex, for example) can be mentioned among the film-forming polymers.

The following examples of film-forming polymers according to the invention can be mentioned:
polycondensates: polyurethanes, acrylic polyurethanes, polyvinylpyrrolidone polyurethanes, polyesters, polyester polyurethanes, polyureas, and mixtures thereof,
polymers obtained by radical polymerization: acrylic and/or vinyl copolymers obtained by (co)polymerization of mono-unsaturated monomers and/or polyethylene monomers such as acrylics, methacrylics, acrylic esters, styrenes, and vinyls, and mixtures thereof. Acrylic/silicone copolymers such as hybrid copolymers can also be mentioned.

According to this invention, the film-forming polymers are distinct from the water-soluble dispersant copolymers that are the object of this invention.

According to this invention, "stability on storage" refers to a composition that, when placed in an oven at 45° C. for three months remains in an identical (or substantially identical) form as that obtained just after formulation. Specifically, the composition is said to be stable on storage if it does not display any of the following instabilities: Dephasing, phase separation, creaming, bleeding, release, deposit or sedimentation.

Another object of this invention regards the use of a copolymer according to the invention to provide storage stability, as defined above, to a cosmetic composition for makeup and/or care of keratinous materials comprising a film-forming polymer and a coloring mineral pigment, and this, notably, when the coloring mineral pigment is present in a concentration between 1% and 30 wt. % relative to the total weight of the composition, and/or when the film-forming polymer is present in a concentration between 0.1% and 30 wt. % relative to the total weight of the composition.

"Keratinous materials" refers to eyelashes, eyebrows, and hairs and/or hair. It is also possible to apply the inventive composition to the skin.

"Anionic monomers having a polymerizable vinyl group and a carboxyl moiety" are negatively charged monomers in a basic aqueous solution. The anionic monomers having a polymerizable vinyl group and a carboxyl moiety are, for example, chosen from among acrylic acid and/or methacrylic acid.

According to one aspect of the present invention, the copolymer comprises "at least one (meth)acrylic acid monomer". "At least one monomer of (meth)acrylic acid" means at least one monomer of acrylic acid or at least one monomer of methacrylic acid. According to this invention, the copolymer may comprise monomers of acrylic acid and/or monomers of methacrylic acid. Therefore, the (meth)acrylic acid skeleton of the inventive copolymer can be made up exclusively of acrylic acid, exclusively of methacrylic acid, or of a mixture of acrylic acid and methacrylic acid.

DETAILED DESCRIPTION OF THE INVENTION

The state of dispersion of the pearlescent pigments and/or coloring mineral pigments, especially those of the iron oxide(s) type, as well as the decreased viscosity of the cosmetic formulations, are linked to the molecular weight, composition, and architecture of the copolymers of the invention.

In particular, the copolymer of the invention has a specific molecular weight between 20,000 and 400,000 g/mol, for example between 20,000 and 250,000 g/mol. The best viscosity values, and therefore the best effect on the homogeneity of the compositions, are in fact obtained in cosmetic compositions comprising copolymers of molecular weight in the middle of this range.

In the context of this invention, "molecular weight" means the weight-average molecular weight or $M_w$. The molecular weight is determined by size exclusion chromatography (SEC), also called gel permeation chromatography (GPC).

According to one embodiment of the present invention, the copolymer has a molecular weight of between 20,000 g/mol and 350,000 g/mol, for example between 30,000 g/mol and 380,000 g/mol, or between 40,000 g/mol and 250,000 g/mol.

In another embodiment of this invention, the copolymer has a molecular weight between 50,000 g/mol and 110,000 g/mol.

In one embodiment of the present invention, the copolymer is such that the R in the macromonomer of formula (I) is a methacrylate group, a methacrylurethane group, an acrylate group, a vinyl group, a methallyl group, or an allyl group.

Said copolymer of the invention is obtained through known conventional free radical copolymerization processes in solution, in direct or inverse dispersion, in bulk, in suspension or precipitation in suitable solvents, in the presence of known initiators and transfer agents; or else, it is obtained through controlled free radical polymerization processes such as the method called Reversible Addition Fragmentation Transfer (RAFT), the method called Atom Transfer Radical Polymerization (ATRP), the method called Nitroxide Mediated Polymerization (NMP), or, finally, the method called Cobaloxime Mediated Free Radical Polymerization.

In one embodiment of the present invention, the copolymer also comprises an ester of (meth)acrylic acid, for example ethyl acrylate.

In one embodiment of the present invention, the copolymer is a (meth)acrylic copolymer and is made up of (expressing the percentage by weight of each of its components):
a) 5% to 30% of at least one monomer of (meth)acrylic acid;
b) 70% to 95% at least one macromonomer having the formula (I);
c) 0% to 20% of at least one monomer which is an ester of (meth)acrylic acid;
where the sum of the percentages a), b), and c) is 100%.

In another embodiment of the present invention, the copolymer is a (meth)acrylic copolymer and is made up of (expressing the percentage by weight of each of its components):
a) 5% to 15% of at least one monomer of (meth)acrylic acid;
b) 85% to 95% at least one macromonomer having the formula (I);
c) 0% to 10% of at least one monomer which is an ester of (meth)acrylic acid;
where the sum of the percentages a), b), and c) is 100%.

In one embodiment of the present invention, the copolymer is such that m and n in formula (I) are between 10 and 90.

According to the invention, said copolymer can be entirely or partially neutralized by one or more neutralization agents having a monovalent or polyvalent cation. Said agents can be chosen, for example, from the group consisting of ammonium hydroxide; calcium or magnesium hydroxides or oxides; sodium, potassium, or lithium hydroxides; primary, secondary, or tertiary aliphatic and/or cyclic amines, such as, for example stearylamine, ethanolamines (mono, di, and triethanolamine), mono and diethylamine, cyclohexylamine, methylcyclohexylamine, aminomethyl propanol, and morpholin.

The copolymer of the invention has a dispersing effect in cosmetic compositions containing pearlescent pigments and/or coloring pigments such as metal oxides, even at high pigment volume concentrations (PVC).

In an embodiment of this invention, the cosmetic composition of the invention has a pigment volume concentration specifically between 15% and 50%.

The "pigment volume concentration" is defined by the following equation:

$$PVC\ (\%) = 100 \times V_c / (V_c + V_1)$$

where $V_c$ represents the volume of the coloring pigments, and
$V_1$ represents the dry volume of the film-forming polymer in the cosmetic composition.

In one embodiment of the present invention, the cosmetic composition comprises 1 to 30 wt % of pearlescent and/or coloring pigment, e.g. 1 to 20 wt % or 1 to 10 wt % (the % ranges are inclusive of the endpoints).

In another embodiment of the present invention, the cosmetic composition comprises 3 to 30 wt % of pearlescent and/or coloring pigment, e.g. 3 to 20 wt % or 3 to 10 wt %.

In another embodiment of the present invention, the cosmetic composition comprises 0.1 to 20 wt. % of a film-forming polymer, e.g. 0.1 to 10 wt %.

According to one embodiment of the present invention, the cosmetic composition for makeup and/or for the care of keratinous material, comprises:
a) from 3 to 25 wt. % of pearlescent and/or coloring pigment;
b) from 8 to 15 wt. % of film-forming polymer; and
c) from 0.05 to 8 wt. % of comb-type copolymer formed of:
 c1) at least one anionic monomer having a polymerizable vinyl group and a carboxyl moiety, such as (meth)acrylic acid, and
 c2) at least one macro-monomer having the formula (I):

wherein:
m and n are two integers other than zero and lower than 150;
PO and EO designate respectively propylene oxide and ethylene oxide and are arranged either randomly or in a regular pattern;
R designates a polymerizable unsaturated group,
R' is hydrogen or an alkyl group having 1-4 carbon atoms;
the molecular weight of said copolymer being between 20,000 g/mol and 400,000 g/mol.

The inventive cosmetic composition may appear in the form of an aqueous continuous phase or in anhydrous form, or in the form of a water-in-oil or oil-in-water emulsion or a water-in-oil or oil-in-water dispersion. It may be solid, liquid, or pasty. The inventive composition may thereby comprise an aqueous phase that may be formed essentially of water.

According to one embodiment of the present invention, these cosmetic compositions are formed of at least two phases, i.e. an aqueous phase and a non-aqueous phase, said phases potentially themselves incorporating solid particles such as pearlescent and/or coloring pigments. The copolymer according to the present invention is generally incorporated into the aqueous phase of the cosmetic composition, but it may be incorporated into the non-aqueous phase.

Thus, according to one embodiment of the present invention, the cosmetic composition comprises, relative to the composition's total weight:
a) 10% to 99.9 wt. % of aqueous phase;
b) 0.1% to 90% based on the total weight of non-aqueous phase;
the sum a)+b) being equal to 100%.

In another embodiment of the present invention, the cosmetic composition comprises, relative to the composition's total weight:
a) 15% to 99.5 wt. % of aqueous phase;
b) 0.5% to 85% based on the total weight of non-aqueous phase;
the sum a)+b) being equal to 100%.

In yet another embodiment of the present invention, the cosmetic composition comprises, relative to the composition's total weight:
a) 50% to 70 wt. % of aqueous phase;
b) 30% to 50% based on the total weight of non-aqueous phase;
the sum a)+b) being equal to 100%.

The aqueous phase of the composition can be made up of a mixture of water and water-miscible organic solvents (miscibility in water greater than 50 wt. % at 25° C.). These solvents are chosen, among for example: the lower monoalcohols comprising 1-5 carbon atoms, such as ethanol and isopropanol; the glycols comprising 2 to 8 carbon atoms such as propylene glycol, ethylene glycol, 1,3-butylene glycol, and dipropylene glycol; the C3-C4 ketones; the C2-C4 aldehydes; and the ethoxylated alcohols.

The non-aqueous phase (or fatty phase) of the cosmetic composition of the present invention may comprise natural or synthetic components not miscible with water, which are liquid at room temperature (25° C.) and/or solid at room temperature; notably, they can be chosen from the category that includes waxes, oils, pasty fatty substances, gums, and mixtures thereof.

"Wax" in the context of the present invention refers to a lipophilic compound that is solid at room temperature (25° C.), may or may not be deformable, can reversibly change between solid and liquid state, with a melting point greater than or equal to 30° C. that may reach as high as 200° C. and particularly up to 120° C. By bringing wax to liquid state (melting point), it is possible to make it miscible to oils and to form a microscopically homogeneous mixture, but when the mixture's temperature is lowered to room temperature, the wax is recrystallized in the mixture's oils. In particular, waxes that comply with the invention may have a melting point greater than or equal to 45° C., and in particular greater than or equal to 55° C.

"Oil" refers to a fatty substance that is liquid at room temperature (25° C.). The oil may be volatile or non-volatile. A volatile oil may evaporate when it comes in contact with the skin or keratinous fiber in less than an hour, at room temperature and atmospheric pressure. A non-volatile oil is an oil that remains on the skin or keratinous fiber at room temperature and atmospheric pressure. for at least several hours. The oil may be chosen from among all physiologically acceptable oils, and particular those that are cosmetically acceptable, particularly mineral, animal, vegetable, and synthetic oils; in particular, hydrocarbon and/or silicone and/or fluorinated volatile or non-volatile oils and mixtures thereof. More specifically, a hydrocarbon oil refers to an oil principally comprising carbon and hydrogen atoms, and potentially one or more groups chosen from among hydroxyl, ester, ether, and carboxyl groups. Volatile oils and non-volatile oils are commercially available.

The inventive composition may comprise wax and/or volatile or non-volatile oils in a concentration ranging from 1 to 80 wt % in relation to the total weight of the composition, e.g. 5 to 70 wt %, or 10 to 50 wt %, or 15 to 40 wt %.

In another embodiment of the present invention, the cosmetic composition comprises 0.05 to 5 wt % of said copolymer as-is, e.g. 0.1 to 5 wt % or 0.1 to 3 wt %.

The composition of the invention may further comprise any additive normally used in cosmetics.

Moreover, the cosmetic composition of the invention may contain one or more of the following ingredients:
  reflecting particles;
  surfactant or emulsifying agents or emulsifiers;
  emollients;
  humectants, hydrating agents;
  neutralizing, acidifying, or alkalizing agents;
  preservatives;
  fillers;
  antioxidants;
  perfumes;
  plasticizers;
  cosmetic active ingredients such as vitamins;
  sunscreens.

These additives may be present in the composition in a concentration of 0.01 to 30% of the total weight of the composition.

For example, the composition may comprise at least one other structuring agent, chosen from among thickening agents, lipophilic gelling agents normally used in cosmetics, and mixtures thereof.

Lipophilic gelling agents normally used in cosmetics include mineral lipophilic gelling agents such as clays or silicas, organic polymer lipophilic gelling agents such as fully or partially cross-linked elastomer organopolysiloxanes, sequenced polystyrene/copoly(ethylene-propylene) copolymers, polyamides, and mixtures thereof. As for the aqueous phase of the composition, it may be thickened by a thickening agent. Aqueous-phase thickening agents that may be used according to the invention include cellulosic thickeners, clays, polysaccharides, acrylic polymers, associative polymers, and mixtures thereof. Hydrophilic thickening agents particularly include AMP S/acrylamide copolymers of the SEPIGEL or SIMULGEL type (SEPPIC).

In the inventive composition, the concentration of aqueous-phase thickening agent may range from 0.1 to 15 wt %, in relation to the total weight of the composition, e.g. from 1% to 10 wt %, or e.g. 1 to 5 wt %.

The composition may also comprise surface-active agents which are non-ionic, anionic, cationic, amphoteric or also surface-active emulsifiers.

The inventive composition may comprise an auxiliary film-forming agent encouraging the formation of a film with the film-forming polymer. Such a film-forming agent may be chosen from among the compounds known to the person skilled in the art to potentially fulfill the desired function, and particularly from among plasticizers and coalescing agents.

The fillers may be chosen from among those well-known to the person skilled in the art and commonly used in cosmetic compositions.

The inventive cosmetic composition for makeup and/or for the care of keratinous material can take the form of a product for the eyelashes, of a product for the eyebrows, or of a makeup product for hair or hairs, more specifically the form of a mascara. It can be in fluid, solid, or two-phase form. It can take, for example, the form of a stick or the form of a soft paste.

This cosmetic composition can be applied over ("top coat") or under ("base coat") the makeup.

EXAMPLES

In each of the following examples, the molecular weight of the copolymers of the invention is determined by size exclusion chromatography (SEC) or gel permeation chromatography (GPC).

Such a technique implements a WATERS™ liquid chromatography instrument equipped with two detectors. One of these detectors combines dynamic/static light scattering at a 90° angle with the measurement of the viscosity performed with a VISCOTEK™ MALVERN™ viscometer. The other detector is a WATERS™ refractometric concentration detector.

This liquid chromatography instrumentation is equipped with size exclusion columns, suitably chosen by the person skilled in the art to separate the polymers under study on the basis of on their molecular weights. The liquid eluent is an aqueous solution containing 1% of $KNO_3$.

In detail, in a first stage, the polymerization solution is diluted to 0.9% based on dry weight in the SEC eluent, which is a 1% solution of $KNO_3$. It is then filtered on a 0.2 μm filter. 100 μL are then injected into the chromatograph (eluent: a 1% solution of $KNO_3$).

The liquid chromatograph contains an isocratic pump (WATERS 515) whose flow rate is set to 0.8 mL/min. The chromatographic instrument also includes a furnace, which, in turn, comprises the following system of columns in series: a GUARD COLUMN ULTRAHYDROGEL WATERS™ precolumn 6 cm long with an interior diameter of 40 mm, an ULTRAHYDROGEL WATERS™ linear column 30 cm long with an interior diameter of 7.8 mm, and two ULTRAHYDROGEL 120 ANGSTROM WATERS™ columns 30 cm long with an interior diameter of 7.8 mm. The detection system, meanwhile, is made up of an RI WATERS™ 410 refractometric detector, and a 270 DUAL DETECTOR MALVERN™ dual detector including a viscometer and 90° light scattering. The temperature of the furnace is brought to 55° C., and that of the refractometer to 45° C.

The chromatography instrument is calibrated with a single PEO 19k standard of the type PolyCAL™ MALVERN™.

Example 1

The copolymers of the present invention are prepared according the methods described below.
Test 1-1
In a 1-liter reactor with mechanical agitation and oil-bath heating, the following were weighed out:
  514 g of water;
  27 g of methacrylic acid;
  217 g of a macromonomer that is a poly(alkylene glycol) methacrylate with molecular weight 3000 and formed of 70 wt % poly(ethylene oxide) and 30 wt % poly(propylene oxide) and
  23 g of water.
In a first container, 1 g of 1,8-dimercapto-3,6-dioxaoctane (DMDO) is weighed out.
In a second container, 1.54 g of ammonium persulfate and 5 g of deionized water are weighed out.

The contents of container 1, then 2, are heated to 65° C. in succession and at once.

The mixture is then baked for 3 hours at 65° C.

The mixture is then neutralized with 50% sodium hydroxide to a pH of 7 and diluted to a concentration of 25% dry material.

The final polymer has the following characteristic: Mw=350,000 g/mol.

Test 1-2

In a 1-liter reactor with mechanical agitation and oil-bath heating, 284 g of water was weighed out:

In a first container, the following are weighed out:
48.7 g of methacrylic acid;
339.5 g of a macromonomer that is a poly(alkylene glycol) methacrylate with molecular weight 3,000 and formed of 70 wt % poly(ethylene oxide) and 30 wt % poly(propylene oxide) and
25.4 g of water.

In a second container, 2.44 g of 1,8-dimercapto-3,6-dioxaoctane (DMDO) is weighed out.

In a third container, a solution of 1.44 g of ammonium persulfate and 80 g of deionized water is weighed out.

The three ingredients from the three containers are brought to 65° C. for three hours in the heated, agitated reactor.

They are then baked for an additional hour at 67° C.

The mixture is then neutralized with 50% sodium hydroxide to a pH of 7 and diluted to a concentration of 40% dry material.

The final polymer has the following characteristic: Mw=71,000 g/mol.

In a third container, a solution of 3.6 g of ammonium persulfate and 80 g of deionized water is prepared.

The ingredients from the three containers are brought to 65° C. for three hours in the heated, agitated reactor. They are then baked for an additional hour at 67° C.

The mixture is then neutralized with 50% sodium hydroxide to a pH of 7 and diluted to a concentration of 40% dry material.

The final polymer has the following characteristic: Mw=45,000 g/mol.

All of the examples 1 to 5 that follow illustrate the use of copolymers according to tests 1-1 to 1-3 in various mascara composition formulations. The figures listed in the last column of the table indicate the weights in grams.

The results (not shown) also indicate that selecting the macromonomer together with the copolymer's molecular weight leads to homogeneous compositions characterized by a decrease in viscosity that do not exhibit any problems (generating heterogeneities, precipitation, depletion, etc.) during the preparation of the mascara and which are stable on storage. It can therefore be deduced that there is a good level of compatibility between the polymer of the invention and the film-forming polymer used in a cosmetic formulation that comprises different black iron oxides or organic pigments.

Example 2

TABLE 1

|  | 2-1 Prior art | 2-2 Invention |
| --- | --- | --- |
| Phase A | | |
| Deionized water | q.s.f. 100 | q.s.f. 100 |
| Black iron oxide (BK 5000 HP - Mineral and Pigment Solutions Inc.) | 7 | 7 |
| Polymer Test 1-1 (quantity as-is) | 0 | 0.1 |
| Preservative | 0.1 | 0.1 |
| Antifoaming agent | 0.1 | 0.1 |
| PEG-200 Glyceryl stearate (Simulsol 220-Seppic) | 4 | 4 |
| Phase B | | |
| Beeswax | 7.4 | 7.4 |
| Carnauba wax | 3.5 | 3.5 |
| Phase C | | |
| Copolymer of acrylamide and sodium acrylamido-2-methylpropane sulfonate in an inverse emulsion in isohexadecane (Simulgel 600 - Seppic) | 3.5 | 3.5 |
| Aqueous dispersion of polyurethane (polycaprolactone/4,4' diphenyl methane diisocyanate) (Disperbond D31W40-Merquinsa) - Film-forming polymer | 8 | 8 |

Test 1-3

In a 1-liter reactor with mechanical agitation and oil-bath heating, 257 g of water was weighed out:

In a first container, the following are weighed out:
50.0 g of acrylic acid;
339.5 g of a macromonomer that is a poly(alkylene glycol) methacrylate with molecular weight 3,000 and formed of 70 wt % poly(ethylene oxide) and 30 wt % poly(propylene oxide) and
21 g of water.

In a second container, 4.45 g of 1,8-dimercapto-3,6-dioxaoctane (DMDO) is weighed out.

The compounds of phase B are melted at 98° C. then homogenized during agitation. Black iron oxide is dispersed in water in the presence of other compounds of phase A. The homogeneous phase A is then heated during moderated agitation to 93° C., then incorporated during heavy agitation into phase B. The mixture is mixed for 5 minutes, then its temperature is lowered to 40° C. Phase C is then incorporated during moderate agitation.

The tests are then cooled to room temperature during moderate agitation, then added to flasks.

A sample of clean, homogeneously colored blond hair is divided in two to conduct mascara tests.

The tests are used to carefully coat the hair. After being coated, the hair is dried using a hair dryer at 65° C. The coloring of the hair samples resulting from the two tests is measured using a surface colorimeter. From the L.a.b measurement, the value L is used to determine the color intensity of each test. The test with the polymer of the invention (example 2-2) shows a color intensity 9% more than the test of the prior art (example 2-1).

Example 3

TABLE 2

|  | 3-1 Prior art | 3-2 Invention |
|---|---|---|
| Phase A | | |
| Deionized water | q.s.f. 100 | q.s.f. 100 |
| Red iron oxide (CG160 - Mineral and Pigment Solutions Inc.) | 6 | 6 |
| Polymer Test 1-2 (quantity as-is) | 0 | 0.1 |
| Preservative | 0.1 | 0.1 |
| Ethanol | 10 | 10 |
| Propylene glycol | 2 | 2 |
| Phase B | | |
| Deionized water | 30 | 30 |
| Polyvinyl alcohol (Selvol PVA 125 - Sekisui) | 1 | 1 |
| Gum arabic | 3 | 3 |
| Hydroxyethyl cellulose (Cellosize HEC QP 300 - Amerchol) | 1.5 | 1.5 |
| Sodium polystyrene sulfonate (Flexan II - Akzo Nobel) | 1 | 1 |
| Copolymer of styrene and acrylate (Joncryl 77 - BASF) - film-forming polymer | 10 | 10 |
| Phase C | | |
| Deionized water | 11.25 | 11.25 |
| Carnauba wax | 5.4 | 5.4 |
| PEG-30 Glyceryl Stearate (Tagat S - Goldschmidt) | 1.35 | 1.35 |
| Ethanol | 2 | 2 |

The PVA, gum arabic, and hydroxyethyl cellulose are dispersed and then dissolved in the water of phase B.

After dissolution, the other compounds of phase B are added and mixed.

The wax and surfactant of phase C are heated to 90° C., then homogenized.

The water of phase C, previously heated to 90° C., is then incorporated into the wax and surfactant mixture, then the whole solution is carefully mixed for 10 minutes, after which the mixture is cooled to 40° C., then the ethanol is added, and after mixing, phase C is cooled to room temperature.

The compounds of phase A are mixed to disperse the red iron oxide.

Phase C and then phase B are added during agitation to the phase A created in this way.

The mixture is homogenized for 10 minutes, then added to a flask.

A sample of clean, homogeneously colored blond hair is divided in two to conduct mascara tests.

The tests are used to carefully coat the hair.

After being coated, the hair is dried using a hair dryer at 40° C.

The coloring of the hair samples resulting from the two tests is measured using a surface colorimeter.

From the L.a.b measurement, the value L is used to determine the color intensity of each test.

The test with the polymer of the invention (example 3-2) shows a color intensity 12% more than the test of the prior art (example 3-1).

Example 4

TABLE 3

|  | 4-1 Prior art | 4-2 Invention |
|---|---|---|
| Phase A | | |
| Deionized water | 5 | 5 |
| Black iron oxide (BK 5000 HP - Mineral and Pigment Solutions Inc.) | 3 | 3 |
| Yellow iron oxide (PURICOLOR Yellow PYE42 - BASF) | 1 | 1 |
| Polymer Test 1-2 (quantity as-is) | 0 | 0.1 |
| Preservative | 0.1 | 0.1 |
| Propylene carbonate | 2 | 2 |
| Phase B | | |
| Paraffin wax | 2.5 | 2.5 |
| Carnauba wax | 6 | 6 |
| Beeswax | 5 | 5 |
| C20-C40 alkyl (hydroxystearyloxy)stearate (Kester Wax K82P - Koster Keunen) | 3.5 | 3.5 |
| Polyethylene wax | 2 | 2 |
| Vinyl polylaurate (Mexomère PP - Chimex) | 0.75 | 0.75 |
| Copolymer of vinyl acetate/allyl stearate (Mexomère PQ - Chimex) - Film-forming polymer | 2.2 | 2.2 |
| Modified hectorite (Bentone 27V - Elementis) | 5.5 | 5.5 |
| Phase C | | |
| Isododecane | q.s.f. 100 | q.s.f. 100 |

The compounds of phase B are melted at 98° C. then homogenized during agitation. Black and yellow iron oxides are dispersed in water in the presence of other compounds of phase A. The homogeneous phase A is then heated during moderated agitation to 93° C., then incorporated during heavy agitation into phase B. The mixture is mixed for 5 minutes, then its temperature is lowered to 70° C. Phase C is then incorporated during moderate agitation. The tests are then cooled to room temperature during moderate agitation, then added to flasks.

A sample of clean, homogeneously colored blond hair is divided in two to conduct mascara tests.

The tests are used to carefully coat the hair. After being coated, the hair is dried using a hair dryer at 65° C. The coloring of the hair samples resulting from the two tests is measured using a surface colorimeter. From the L.a.b measurement, the value L is used to determine the color intensity of each test. The test with the polymer of the invention (example 4-2) shows a color intensity 14% more than the test of the prior art (example 4-1).

Example 5

TABLE 4

|  | 5-1 Prior art | 5-2 Invention |
|---|---|---|
| Phase A | | |
| Deionized water | q.s.f. 100 | q.s.f. 100 |
| Green organic pigment (Vibracolor Green PGR7 - BASF) | 0.5 | 0.5 |

TABLE 4-continued

|  | 5-1 Prior art | 5-2 Invention |
|---|---|---|
| Blue organic pigment (Vibracolor Blue PBL 15:3-L - BASF) | 4.5 | 4.5 |
| Polymer Test 1-3 (quantity as-is) | 0 | 0.1 |
| Preservative | 0.1 | 0.1 |
| Simethicone (antifoaming agent) | 0.4 | 0.4 |
| Phase B | | |
| Candelilla wax - Binder | 24 | 24 |
| Vinylpyrrolidone Copolymer - Eicosene (Ganex V220 - Ashland) - film-forming polymer | 1 | 1 |
| Secondary alkyl sulfonate C14-C17 (Hostapur SAS - Clariant) | 5 | 5 |
| Phase C | | |
| Hydroxyethyl cellulose (Cellosize HEC QP 300 - Amerchol) | 0.9 | 0.9 |

The Candelilla wax of phase B is melted to 80° C., then the copolymer of VP-Eicosene and Hostapur SAS 60 is added and mixed during agitation. The blue and green organic pigments are dispersed in water in the presence of other compounds of phase A. The homogeneous phase A is then heated during moderated agitation to 75° C., then incorporated during heavy agitation into phase B. The mixture is mixed for 5 minutes, then its temperature is lowered to 40° C. Phase C is then incorporated during moderate agitation. The tests are then cooled to room temperature during moderate agitation, then added to flasks.

A sample of clean, homogeneously colored blond hair is divided in two to conduct mascara tests.

The tests are used to carefully coat the hair. After being coated, the hair is dried using a hair dryer at 65° C. The coloring of the hair samples resulting from the two tests is measured using a surface colorimeter. From the L.a.b measurement, the value L is used to determine the color intensity of each test. The test with the polymer of the invention (example 5-2) shows a color intensity 17% more than the test of the prior art (example 5-1).

Example 6

A mascara composition is prepared, using the ingredients listed in the table below. The figures listed in the last column of the table indicate the weights in grams.

TABLE 5

| A | A-1 Deionized Water | q.s.f. 100 |
|---|---|---|
|  | A-2 Methylparaben NF (Protameen) | 0.10 |
|  | A-3 Methocel 40-202 (Dow Chemical) | 0.20 |
|  | A-4 triethanolamine (99%) | 2.80 |
|  | A-5 DL Panthenol USP (DSM) | 0.50 |
|  | A-6 Avalure UR 450 (Lubrizol) | 6.00 |
|  | A-7 PVP K-30 (ISP) | 2.00 |
|  | A-8 Polymer additive as is | 0 or 3.00 |
| B | B-8 Iron Oxide Black 34PC3068 (Emerald Hilton Davis) | 10.00 |
| C | C-9 Emersol 132 (Cognis) | 5.50 |
|  | C-10 Bayberry wax (F. B. Ross) | 1.80 |
|  | C-11 Protachem GMS 450 (Protameen) | 1.70 |
|  | C-12 Beeswax white (F. B. Ross) | 4.50 |
|  | C-13 Carnauba wax N° 1 | 2.70 |
|  | C-14 WW Gum Rosin (Akzo) | 1.80 |
|  | C-15 Propylparaben NF (Protameen) | 0.10 |
| D | D-16 Mirasil SM (Rhodia) | 0.10 |
|  | D-17 Lipovol WGO (Clariant) | 0.10 |
|  | D-18 Phenonip (Clariant) | 0.10 |
|  | D-19 Germaben II (ISP) | 0.50 |

Phase A (Aqueous Phase):

A-1 is agitated and heated to 40° C., then A-2 is dissolved into A-1. The agitation is stopped, then A-3 is added. Agitation continues until a homogeneous mixture is obtained. The triethanolamine A-4 is added to the mixture. A-5 and then the film-forming polymer A-6 (6 wt. %) are then incorporated under agitation. Finally, the film-forming polymer A-7 (2 wt. %) and possibly a 40% solution of the active material of the polymer A-8 (3 wt. % of the polymer as is, or 1.2 wt. % dry weight) are added. After complete homogenization is achieved, the temperature is raised to 75° C.

Phases B (Non-Aqueous Phase), C & D:

All ingredients of phase C are mixed at a temperature of 75° C. The coloring mineral pigment B-8 (10 wt. %) is incorporated. Mixing is continued and the temperature is lowered to 50° C. The ingredients D-16, D-17, D-18, and D-19 are introduced, while still stirring.

Finally, the aqueous phase A is mixed with the blend of the phases B, C, and D. A formulation of the type water-in-oil is therefore obtained.

Test 6-1

This test represents the standard; it does not implement any additional A-8 ingredient besides those mentioned in the table.

Test 6-2

This test represents the prior art and implements, as A-8 ingredient, a polymer made up of 100% acrylic acid, entirely neutralized with sodium hydroxide, and having a weight-averaged molecular weight of 4,500 g/mol.

The polymers of tests 6-3 to 6-7 are prepared according to a method similar to that of tests 1-1 to 1-3 of example 1.

Test 6-3

This test represents the use of a polymer outside of the invention. It uses as A-8 ingredient, a copolymer made up of each of its monomers in the respective percentages:

a) 8.14% of acrylic acid;
b) 2.79% of methacrylic acid; and
c) 89.07% of a monomer having the formula (I):

$$R-(PO)_m-(EO)_n-R'  \quad (I)$$

m=15, n=46;

PO and EO designate respectively propylene oxide and ethylene oxide;

R designates the methacrylate group;

R' represents hydrogen;

completely neutralized with sodium hydroxide (NaOH), and having a molecular weight $M_w$ of 1,800,000 g/mol.

Test 6-4

This test represents the invention and implements a copolymer made up of each of its monomers in the respective percentages by weight:

a) 7.5% of methacrylic acid; and
b) 92.5% of a monomer having the formula (I):

$$R-(PO)_m-(EO)_n-R'  \quad (I)$$

m=15, n=46;

PO and EO designate respectively propylene oxide and ethylene oxide;

R designates the methacrylate group;

R' represents hydrogen;

completely neutralized with sodium hydroxide, and having a molecular weight $M_w$ of 120,000 g/mol.

Test 6-5

This test represents the invention and implements a copolymer made up of each of its monomers in the respective percentages by weight:
a) 12.5% of methacrylic acid;
b) 87.5% of a monomer having the formula (I):

m=15, n 46;
PO and EO designate respectively propylene oxide and ethylene oxide;
R designates the methacrylate group;
R' represents hydrogen;
completely neutralized with sodium hydroxide, and having a molecular weight $M_w$ of 75,000 g/mol.

Test 6-6

This test represents the invention and implements a copolymer made up of each of its monomers in the respective percentages by weight:
a) 12.8% of acrylic acid;
b) 87.2% of a monomer having the formula (I):

m=15, n=46;
PO and EO designate respectively propylene oxide and ethylene oxide;
R designates the methacrylate group;
R' represents hydrogen;
completely neutralized with sodium hydroxide, and having a molecular weight $M_w$ of 45,000 g/mol.

Test 6-7

This test represents the use of a polymer outside of the invention. It implements a copolymer made up of each of its monomers in the respective percentages by weight:
a) 5.1% of acrylic acid and
b) 94.9% of a monomer having the formula (I):

m=0, n=113;
EO designated ethylene oxide;
R designates the methacrylate group;
R' designates the methyl radical;
completely neutralized with sodium hydroxide, and having a weight-averaged molecular weight $M_w$ of 65,000 g/mol.

Viscosity Measurement

The viscosities are measured with a Brookfield model RVT viscometer. Each one of the mascara formulations is contained in standard glass flasks. Each one of the formulations is left to rest for 24 hours at 25° C. before its viscosity is measured. The spindle must be centered relative to the flask's opening and is dipped until the surface of the formulation is flush with the benchmark.

The viscosity is then measured at 20 rpm. The rotation is continued until the viscosity reading is stable.

Preparation of Mascaras and Assessment of their Organoleptic Properties

Each formulation is prepared as described above. The organoleptic properties are observed at room temperature. The following criteria are taken into account: Spread (coverage), Texture (smooth, presence of lumps, granules, "custard like" or stringy appearance), Smell (whether a smell develops or not), Color (change in the homogeneity of the color), Surface (smooth or not).

Stability of Mascaras on Storage:

Each one of the mascara formulations is contained in a suitable 120 ml glass flask. The flasks are then placed into an oven at 45° C. At time=3 months, the flasks are removed from the oven and the following potential instabilities are observed: dephasing or phase separation, creaming, bleeding, release, deposition or sedimentation.

TABLE 6

| Test | Reference/ PA/Invention/ Outside Invention | Brookfield Viscosity (cPs, 20 rpm, 25° C.) | Preparation & Organoleptic properties | Stability on storage Ageing for 3 months at 45° C. |
|---|---|---|---|---|
| 6-1 | REF | 14,610 | * Preparation Stable * Organoleptic: Spread: Nothing to report Texture: Nothing to report Smell: Nothing to report Color: Nothing to report Surface: Nothing to report Conclusion: Stable | Beginning of sedimentation - Bleeding |
| 6-2 | PA | Not measurable | * Preparation: unstable Flocculation & Depletion * Organoleptic: NA Conclusion: Unstable | NA* |
| 6-3 | O-IN | 14,050 | * Preparation Stable *Organoleptic: Spread: Nothing to report Texture: grainy Smell: Nothing to report Color: Nothing to report Surface: Nothing to report Conclusion: slightly unstable | Sedimentation - release |
| 6-4 | INV | 11,550 | * Preparation Stable * Organoleptic: Spread: Nothing to report Texture: Nothing to report Smell: Nothing to report Color: Nothing to report Surface: Nothing to report Conclusion: Stable | Stable - Nothing to report |
| 6-5 | INV | 9,230 | * Preparation Stable * Organoleptic: Spread: Nothing to report Texture: Nothing to report Smell: Nothing to report Color: Nothing to report Surface: Nothing to report Conclusion: Stable | Stable - Nothing to report |
| 6-6 | INV | 10,140 | * Preparation Stable * Organoleptic: Spread: Nothing to report Texture: Nothing to report Smell: Nothing to report Color: Nothing to report Surface: Nothing to report Conclusion: Stable | Stable - Nothing to report |
| 6-7 | O-IN | 16,200 | * Preparation Stable * Organoleptic: Spread: Nothing to report Texture: grainy Smell: Nothing to report Color: Nothing to report Surface: non-smooth Conclusion: slightly unstable | Sedimentation - Bleeding |

* NA: not applicable

The results of Table 6 show that the twin selection made on the choice of macromonomer on the one hand, and on the copolymer's molecular weight on the other leads to homogeneous compositions characterized by a decrease in the viscosity (all values lower than 14,000 cPs) which do not display any problems (generation of heterogeneities, precipitation, depletion . . . ) during the preparation of the mascara and which are stable on storage.

It can therefore be deduced that there is a good level of compatibility between the polymer of the invention and the film-forming polymer used in a cosmetic formulation that comprises 10 wt. % of iron oxide.

Example 7

Variation of the Amount of Coloring Mineral Pigment in the Cosmetic Composition A waterproof mascara composition is prepared using the following ingredients (the figures in the last column indicate the weights in grams):

TABLE 7

| A | A-1 Beeswax (Koster Keunen Inc) | 5.00 |
|---|---|---|
|   | A-2 Carnauba wax (Koster Keunen Inc) | 5.00 |
|   | A-3 Candelilla wax (Koster Keunen Inc) | 3.00 |
|   | A-4 Stearic Acid (Masso) | 2.00 |
|   | A-5 Glyceryl Stearate (Masso) | 1.20 |
|   | A-6 Isopropyl Palmitate (Stéarinerie Dubois) | 3.00 |
|   | A-7 Petrolatum | 4.00 |
|   | A-8 DC 245 (Dow Corning) | 3.00 |
| B | B-9 Carbopol ® ETD 2050 (Lubrizol ™) | 0.10 |
|   | B-10 Veegum ® Ultra (R. T. Vanderbilt) | 0.50 |
|   | B-11 Phenonip ® (Clariant) | 0.90 |
|   | B-12 Iron Oxide Black 34-PV-3069 (Emerald Hilton Davis) | z |
|   | B-13 Deionized Water | q.s.f. 100 |
|   | B-14 Avalure UR 450 (Lubrizol ™) | 15.00 |
|   | B-15 DC 193 Surfactant (Dow Corning) | 64.00 |
|   | B-16 Polymer additive as is | 3.00 |
| C | C-16 triethanolamine (99%) | q.s.f. pH 7.5 |

First of all, B-9, B-10, B-13, and possibly the polymer additive B-16 (3 wt. % as is of the total weight of the cosmetic composition) are blended (800 to 1,000 rpm for 60 minutes) at room temperature.

Then, the compounds B-11, B-12, the film-forming polymer B-14 (14 wt. % of the total weight of the cosmetic composition), and B-15 are added. The mixture is homogenized. This mixture of phase B is heated to 60° C.

At the same time, all ingredients of the A phase (except the ingredient A-8) are blended and the mixture is heated to 85° C. The ingredient A-8 is then added to this mixture.

The non-aqueous phase A is incorporated into the aqueous phase B and the blend is homogenized. The water evaporated is restored. The pH is adjusted to 7.5 with ingredient C-16.

The blend left to cool while stirring. A formulation of the oil-in-water type has thus been prepared.

Test 7-1

This test represents the standard; it does not implement any additional B-16 ingredient besides those mentioned in Table 7.

Test 7-2

This test represents the prior art and implements, as the B-16 ingredient a polymer made up of 100% acrylic acid, entirely neutralized with sodium hydroxide, and having a weight-averaged molecular weight of 4,500 g/mol.

Test 7-3

This test represents the invention and implements as a B16 ingredient a copolymer made up of each of its monomers in the respective percentages:

a) 12.5% of methacrylic acid;
b) 87.5% of a monomer having the formula (I):

$$R\text{---}(PO)_m\text{-}(EO)_n\text{---}R' \quad (I)$$

m=15, n=46;
PO and EO designate respectively propylene oxide and ethylene oxide;
R designates the methacrylate group;
R' represents hydrogen;
completely neutralized with sodium hydroxide, and having a weight-averaged molecular weight Mw of 75,000 g/mol.

TABLE 8

| Test | Z (wt. %) | Brookfield Viscosity (cPs, 20 rpm, 25° C.) | Preparation & Organoleptic properties | Stability on storage Ageing for 3 months at 45° C. |
|---|---|---|---|---|
| 7-1 REF | 3 | 15,270 | * Preparation: Stable<br>* Organoleptic:<br>Spread: Nothing to report<br>Texture: Nothing to report<br>Smell: Nothing to report<br>Color: Nothing to report<br>Surface: Nothing to report<br>Conclusion: Stable | Stable - Nothing to report |
|  | 12 | 120,310 | * Preparation: Stable<br>* Organoleptic:<br>Spread: Nothing to report<br>Texture: grainy<br>Smell: Nothing to report<br>Color: Nothing to report<br>Surface: Nothing to report<br>Conclusion: slightly unstable | Beginning of sedimentation |
|  | 25 | Not measurable | NA | Not measurable |
| 7-2 PA | 3 | Not measurable | * Preparation: unstable<br>Flocculation & Depletion<br>* Organoleptic: NA<br>Conclusion: Unstable | NA |
|  | 12 | Not measurable | * Preparation: unstable<br>Flocculation & Depletion<br>* Organoleptic: NA<br>Conclusion: Unstable | NA |
|  | 25 | Not measurable | * Preparation: unstable<br>Flocculation & Depletion<br>* Organoleptic: NA<br>Conclusion: Unstable | NA |
| 7-3 INV | 3 | 10,810 | * Preparation: Stable<br>* Organoleptic:<br>Spread: Nothing to report<br>Texture: Nothing to report<br>Smell: Nothing to report<br>Color: Nothing to report<br>Surface: Nothing to report<br>Conclusion: Stable | Stable - Nothing to report |
|  | 12 | 60,180 | * Preparation: Stable<br>* Organoleptic:<br>Spread: Nothing to report<br>Texture: Nothing to report<br>Smell: Nothing to report<br>Color: Nothing to report<br>Surface: Nothing to report<br>Conclusion: Stable | Stable - Nothing to report |
|  | 25 | 112,180 | * Preparation: Stable<br>* Organoleptic:<br>Spread: Nothing to report<br>Texture: Nothing to report<br>Smell: Nothing to report<br>Color: Nothing to report<br>Surface: Nothing to report<br>Conclusion: Stable | Stable - Nothing to report |

The results of Table 8 show that using the copolymer of the invention in a waterproof mascara formulation makes it possible to homogenize and to reduce the viscosity while maintaining stability in the course of the implementation and of the ageing test; this also applies to the formulations comprising 12% and 25% by weight of iron oxides.

Therefore, it can be deduced that there is a good level of compatibility between the polymer of the invention and the film-forming polymer.

The invention claimed is:
1. A cosmetic composition, comprising:
a) from 1 to 20 wt. % of a coloring mineral pigment;
b) from 0.1 to 30 wt. % of a film-forming polymer; and
c) from 0.05 to 8 wt. % of a water-soluble comb copolymer
wherein the water-soluble comb copolymer comprises:
c1) an anionic monomer having a polymerizable vinyl group and a carboxyl moiety, and
c2) a macro-monomer having the formula (I):

and wherein:
m and n are integers other than zero and less than or equal to 150;
PO and EO are respectively propylene oxide and ethylene oxide and are arranged either randomly or in a regular pattern;
R is a polymerizable unsaturated group,
R' is hydrogen or an alkyl group having 1-4 carbon atoms; and
a molecular weight of the water-soluble comb copolymer is between 20,000 g/mol and 400,000 g/mol,
and wherein said cosmetic composition is homogeneous.

2. The cosmetic composition according to claim 1, comprising:
a) from 1 to 20 wt. % of the coloring mineral pigment;
b) from 0.1 to 30 wt. % of the film-forming polymer; and
c) from 0.5 to 8 wt. % of the water-soluble comb copolymer,
wherein the water-soluble comb copolymer comprises:
c1) a monomer of (meth)acrylic acid and
c2) the macro-monomer, and
the molecular weight of the water-soluble comb copolymer is between 20,000 g/mol and 250,000 g/mol.

3. The cosmetic composition according to claim 1, further comprising:
1 to 80 wt. % of a volatile or non-volatile wax or oil.

4. The cosmetic composition according to claim 1, comprising:
2 to 5 wt. % of the water-soluble comb copolymer, and
0.5% to 20 wt. % of the film-forming polymer.

5. The cosmetic composition according to claim 1, further comprising:
0.1% to 15 wt. % of an aqueous-phase thickening agent.

6. The cosmetic composition according to claim 1, further comprising:
at least one additive selected from the group consisting of reflective particles, a surfactant, an emulsifier, an emollient, a humectant, a hydrating agent, a neutralizing, acidifying, or alkalizing agent, a preservative, a filler, an antioxidant, a perfume, a plasticizer, a cosmetic active ingredient, and a sunscreen.

7. The cosmetic composition according to claim 1, further comprising water.

8. The cosmetic composition according to claim 1, wherein said cosmetic composition is a composition for makeup of keratinous material.

9. The cosmetic composition according to claim 7, wherein said cosmetic composition is a composition for makeup of keratinous material.

10. The cosmetic composition according to claim 1, wherein said cosmetic composition is a mascara.

11. The cosmetic composition according to claim 7, wherein said cosmetic composition is a mascara.

12. The cosmetic composition according to claim 1, comprising:
a) from 1 to 20 wt. % of iron oxide or a mixture of iron oxides;
b) from 0.1 to 30 wt. % of said film-forming polymer; and
c) from 0.05 to 8 wt. % of said water-soluble comb copolymer,
wherein the anionic monomer having a polymerizable vinyl group and a carboxyl moiety is a monomer of (meth)acrylic acid, and R in the macromonomer of formula (I) is a methacrylate group, a methacrylurethane group, an acrylate group, a vinyl group, a methallyl group, or an allyl group.

13. The cosmetic composition according to claim 12, further comprising water.

14. The cosmetic composition according to claim 13, wherein said cosmetic composition is a composition for makeup of keratinous material.

15. The cosmetic composition according to claim 13, wherein said cosmetic composition is a mascara.

16. The cosmetic composition according to claim 15, wherein the macromonomer of formula (I) is a methacrylate group.

17. The cosmetic composition according to claim 1, wherein the cosmetic composition has a pigment volume concentration PVC between 15% and 50%.

18. The cosmetic composition according to claim 11, wherein the cosmetic composition has a pigment volume concentration PVC between 15% and 50%.

19. The cosmetic composition according to claim 15, wherein the cosmetic composition has a pigment volume concentration PVC between 15% and 50%.

20. The cosmetic composition according to claim 1, wherein the coloring mineral pigment is chosen from iron oxides, chromium oxides, zirconium oxides, zinc or cerium oxides, manganese violet, chromium hydrate, and iron blue.

21. A cosmetic composition, comprising:
a) from 1 to 20 wt. % of a pigment selected from blue ultramarine and carbon black;
b) from 0.1 to 30 wt. % of a film-forming polymer; and
c) from 0.05 to 8 wt. % of a water-soluble comb copolymer
wherein the water-soluble comb copolymer comprises:
c1) an anionic monomer having a polymerizable vinyl group and a carboxyl moiety, and
c2) a macro-monomer having the formula (I).

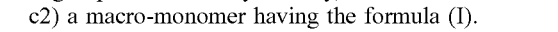

and wherein:
m and n are integers other than zero and less than or equal to 150;
PO and EO are respectively propylene oxide and ethylene oxide and are arranged either randomly or in a regular pattern;
R is a polymerizable unsaturated group,
R' is hydrogen or an alkyl group having 1-4 carbon atoms; and
a molecular weight of the water-soluble comb copolymer is between 20,000 g/mol and 400,000 g/mol,
and wherein said cosmetic composition is homogeneous.

* * * * *